United States Patent [19]

Tanaka et al.

[11] Patent Number: 5,681,710

[45] Date of Patent: Oct. 28, 1997

[54] REAGENT FOR DETERMINING (1→3)-β-D-GLUCAN

[75] Inventors: Shigenori Tanaka; Hiroshi Tamura; Makoto Ohki, all of Tokyo, Japan

[73] Assignee: Seikagaku Kogyo Kabushiki Kaisha, Tokyo, Japan

[21] Appl. No.: 391,097

[22] Filed: Feb. 21, 1995

Related U.S. Application Data

[63] Continuation of Ser. No. 949,560, filed as PCT/JP92/00311, Mar. 13, 1992, abandoned.

[30] Foreign Application Priority Data

Mar. 14, 1991 [JP] Japan ................................. 3-073651
Mar. 14, 1991 [JP] Japan ................................. 3-073652

[51] Int. Cl.[6] ................... C12Q 1/56; C12Q 1/00; C12Q 1/34; C12Q 1/44
[52] U.S. Cl. ................... 435/13; 435/4; 435/18; 435/19; 435/23; 435/24; 435/34; 436/63; 436/74
[58] Field of Search ................ 435/13, 4, 18, 435/19, 23, 34, 7.21, 24; 436/63, 74

[56] References Cited

U.S. PATENT DOCUMENTS

| | | | |
|---|---|---|---|
| 4,606,824 | 8/1986 | Chu et al. | 422/161 |
| 4,970,152 | 11/1990 | Ashida et al. | 435/19 |
| 5,047,353 | 9/1991 | Tsuchiya et al. | 435/18 |
| 5,155,032 | 10/1992 | Tanaka et al. | 435/18 |
| 5,179,006 | 1/1993 | Matuura et al. | 435/18 |
| 5,266,461 | 11/1993 | Tanka | 435/7.21 |

FOREIGN PATENT DOCUMENTS 2138193 5/1990 Japan.
WO8302123 6/1993 WIPO.

OTHER PUBLICATIONS de Gruyter, Concise Encyclopedia of Biochemistry, Berlin, 1983, p. 125.

Clinica Chimica Acta, vol. 149, 1985, pp. 55–65, "A New Chromogenic Endotoxin–Specific Assay Using Recombined Limulus Coagulation Enzymes And Its Clinical Applications", Taminori Obayashi et al.

Primary Examiner—John Kight
Assistant Examiner—Louise N. Leary
Attorney, Agent, or Firm—Sughrue, Mion, Zinn, Macpeak & Seas

[57] ABSTRACT

The present invention provides a reagent for determining (1→3)-β-D-glucan comprising a lysate substantially free from any endotoxin-sensitive factor, which is obtained by contacting limulus amebocyte lysate optionally containing dextran with a polyamide or cellulose insoluble carrier, which makes it possible to rapidly and easily determine at a high accuracy (1→3)-β-D-glucan of mycotic origin contained in the body fluid such as blood or urine.

6 Claims, 2 Drawing Sheets

REAGENT FOR DETERMINING (1→3)-β-D-GLUCAN

This is a Continuation of application Ser. No. 07/949,560 filed as PCT/JP92/00311 Mar. 13, 1992, now abandoned.

TECHNICAL FIELD

The present invention relates to a reagent for determining (1→3)-β-D-glucan using limulus (horseshoe crab) amebocyte lysate and a method for detecting a mycete.

TECHNICAL BACKGROUND

A method of determining endotoxin using limulus amebocyte lysate (hereinafter abbreviated as lysate) is known which is commonly called the limulus test. This method utilizes the coagulation of the lysate with a trace amount of endotoxin. The subsequent biochemical studies reveal that the coagulation reaction is caused by a step-wise activation of several coagulation factors [Takanori Nakamura et al., Japanese Journal of Bacteriology, 38, 781–803 (1983)]. This reaction is illustrated below by reference to FIG. 1 with the use of lysate obtained from *Tachypleus tridentatus* in Japan by way of example. When endotoxin is added to the lysate, factor C (endotoxin-sensitive factor, molecular weight: 123,000) is activated to form an activated factor C. This activated factor C restrictedly hydrolyzes factor B (molecular weight: 64,000) at specific sites so as to form an activated factor B. This activated factor B then activates a proclotting enzyme (molecular weight: 54,000) and thus change it into a clotting enzyme. The clotting enzyme thus formed restrictedly hydrolyzes specific sites (i.e., $Arg^{18}$-$Thr^{19}$ and $Arg^{46}$-$Gly^{47}$) in the loop crosslinked via disulfide bonds of coagulogen (coagulating protein, molecular weight: 19,723) to thereby liberate a peptide C (consisting of 28 amino acid residues) represented by H-$Thr^{19}$ - - - $Arg^{46}$-OH, while the residual part of the coagulogen is converted into a coagulin gel. Thus, this reaction comprises a series of reactions (a cascade reaction system).

When not only endotoxin but also (1→3)-β-D-glucan is added to the lysate, on the other hand, the factor G in this cascade reaction system shown in FIG. 1 is activated. Then the activated factor G thus formed activates the proclotting enzyme into the clotting enzyme. Subsequently, the reaction proceeds in the same manner as described above so as to form a coagulin gel.

The clotting enzyme formed in the above-mentioned cascade reaction system liberates p-nitroaniline from, for example, t-butoxycarbonyl-leucyl-glycyl-arginine-p-nitroanilide (Boc-Leu-Gly-Arg-pNA) which is separately added to the reaction system. Thus endotoxin or (1→3)-β-D-glucan can be quantitatively determined by measuring the absorbance of the produced p-nitroaniline which is a chromogenic substance. This cascade reaction system is applied to the specific determination of (1→3)-β-D-glucan in Examples described below.

On the other hand, a method for determining (1→3)-β-D-glucan using factor G in the lysate has been reported [Obayashi, T. et al., Clin. Chim. Acta, 149, 55–65 (1985)].

However this method comprises fractionating the lysate by gel filtration or affinity chromatography using a carrier having heparin or dextran sulfate fixed thereon to remove endotoxin-sensitive factor, i.e., factor C, and determining (1→3)-β-D-glucan exclusively with the factor G and proclotting enzyme. Thus, this method requires extremely complicated procedures for the above-mentioned fractionation.

DISCLOSURE OF THE INVENTION

The present invention provides a reagent for determining (1→3)-β-D-glucan comprising a processed lysate substantially free from any endotoxin-sensitive factor (factor C), which is obtained by treating lysate through an improved method.

The reagent for determining (1→3)-β-D-glucan according to the present invention comprises a processed limulus amebocyte lysate substantially free from any endotoxin-sensitive factor and containing at least an ingredient specifically reactive with (1→3)-β-D-glucan as a main component, which is obtainable by contacting a solution containing limulus amebocyte lysate with an adsorbent capable of specifically adsorbing an endotoxin-sensitive factor.

As the above-mentioned adsorbent capable of specifically adsorbing an endotoxin-sensitive factor, a polyamide insoluble carrier or a cellulose insoluble carrier may be preferably employed. The reagent may preferably contain dextran. Further, the reagent may preferably contain a divalent metal salt effective in the activation of the cascade reaction system, optionally together with the substrate of the clotting enzyme.

The present invention further provides a method for producing a reagent for determining (1→3)-β-D-glucan which comprises contacting a solution containing limulus amebocyte lysate with an adsorbent capable of specifically adsorbing an endotoxin-sensitive factor to thereby give a processed limulus amebocyte lysate substantially free from any endotoxin-sensitive factor and contains at least an ingredient capable of specifically reacting with (1→3)-β-D-glucan.

In the above-mentioned production method, it is preferable that the solution containing limulus amebocyte lysate further contains dextran.

The present invention further provides a method for producing a reagent for determining (1→3)-β-D-glucan which comprises adding a divalent metal salt effective in the activation of the cascade reaction system optionally together with a substrate of a clotting enzyme, to the processed limulus amebocyte lysate and drying the resulting mixture under unheated conditions.

The present invention furthermore provides a method for detecting mycetes which comprises reacting a body fluid of a patient suffering from mycosis with the above-mentioned reagent for determining (1→3)-β-D-glucan and measuring changes in the substrates in the cascade reaction system thus caused by (1→3)-β-D-glucan.

Usable as the lysate is blood cell extracts prepared from hemolymph of horseshoe crab including *Limulus polyphemus* in America, *Tachypleus tridentatus* in Japan and China, *Tachypleus gigas* in Thailand and Malaysia, *Carcinoscorpius rotundicauda* in Thailand and Malaysia in a conventional manner (ex., J. Biochem., 80, 1011–1021 (1976)).

The limulus amebocyte lysate may be contacted with a polyamide or cellulose insoluble carrier either continuously or batchwise, for example, by passing the lysate through said carrier in the form of a membrane and then collecting the passed fraction, by passing the lysate through a column packed with said carrier in the form of particles and then collecting the passed fraction or by contacting the lysate with said carrier in the form of tips or a powder of an appropriate size and then eliminating the carrier by a common solid/liquid separation procedure such as centrifugation or filtration.

The adsorption of endotoxin-sensitive factors by the carrier can be further promoted by adding dextran to the lysate prior to the contact of the lysate with the carrier, as well as the sensitivity of the processed lysate thus obtained to (1→3)-β-D-glucan.

The average molecular weight of the dextran to be used ranges from 5,000 to 5,000,000, preferably from 10,000 to 100,000.

Dextran having an average molecular weight less than 5,000 cannot be used since it hardly promotes the adsorption of endotoxin-sensitive factors by the carrier. On the other hand, one having an average molecular weight exceeding 5,000,000 cannot be used since it has an excessively high viscosity.

The polyamide insoluble carrier to be used in the present invention is a crystalline liner polymer having a main chain consisting of repeated acid amide bonds and in the form of membrane (e.g., filter, hollow fiber, tube, film), particles, tips or powder. Examples thereof include carriers comprising a diamine/dicarboxylic acid polycondensate or a compound formed by polycondensing ω-amino-carboxylic acid or the corresponding lactam such as nylon 6 or nylon 66 as the main component.

The cellulose insoluble carrier to be used in the present invention is a carrier comprising cellulose or a derivative thereof as the main component and in the form of membrane (e.g., filter, hollow fiber, tube, film), particles, tips or powder, as described above. Examples of the cellulose derivative include cellulose esters such as cellulose acetate or cellulose nitrate, aminoethyl-, bromoacetyl-, phospho- or carboxymethyl-substituted cellulose and carboxymethylcellulose hydrazide derivative.

Biological samples to be assayed for $(1\rightarrow3)$-$\beta$-D-glucan in accordance with the present invention include body fluid, exudate and excretion such as blood, plasma, serum, cerebrospinal fluid, ascites, articular fluid, pleuritic fluid, milk and urine.

$(1\rightarrow3)$-$\beta$-D-glucan may be determined using the reagent of the present invention by the conventional method for determining the activity of the clotting enzyme formed through the activation in the cascade reaction system shown in FIG. 1.

In order to determine the amidolytic activity of the clotting enzyme, the above-mentioned synthetic peptide substrate having a chromogenic residue or those having the similar amino acid sequence except that the carboxyl group of arginine at the C-terminal is substituted not with the above-mentioned chromogenic residue but with a known fluorescent residue, luminescent residue or ammonia via an amide bond may be used as a substrate. Thus the amidolytic activity can be measured by determining the product formed from the synthetic substrate through the reaction with the clotting enzyme. More particularly, the above-mentioned synthetic peptide substrate is added to a reaction system including the reagent of the present invention and $(1\rightarrow3)$-$\beta$-D-glucan and a chromogenic or fluorescent product or ammonia formed by the reaction (the cascade reaction, optionally followed by conversion of the product into another dye) is determined with, for example, a spectrophotometer, a fluorophotometer, a chemiluminescence detection device or an electrode for detecting ammonia (JP-A-62-148860).

The protease activity of the clotting enzyme can be determined by measuring the gelation reaction in which the clotting enzyme reacts with a coagulogen (substrate) contained in the reagent of the present invention (or separately added thereto) so as to form a coagulin gel with an appropriate apparatus (for example, turbidimeter, visco-meter) or with naked eyes.

The processed limulus amebocyte lysate to be used in the assay according to the present invention is required to be combined with a divalent metal salt effective in the activation of the above-mentioned cascade reaction system. Examples of the divalent metal salt include halides (e.g., chlorides) and sulfates of alkaline earth metals such as magnesium, calcium and strontium. The reagent of the present invention may be prepared by drying the processed limulus amebocyte lysate together with the above-mentioned divalent metal salt under unheated conditions (for example, lyophilization) to a solid state. A reagent for determining the above-mentioned amidolytic activity preferably comprises the above-mentioned synthetic peptide substrate, in addition to the above-mentioned divalent metal salt, and it may be optionally dried.

FUNCTION

According to the present invention, endotoxin-sensitive factors contained in the lysate can be adsorbed and eliminated, without deteriorating the activity of any $(1\rightarrow3)$-$\beta$-D-glucan-sensitive factor, simply by contacting the lysate with a polyamide or cellulose insoluble carrier and thus a processed lysate capable of specifically reactive with $(1\rightarrow3)$-$\beta$-D-glucan can be obtained. In addition, the adsorbing/eliminating effect can be further elevated by adding dextran to the lysate in advance or in the step of contacting the lysate with the carrier so as to increase the viscosity of the lysate.

BEST MODE TO PRACTICE THE INVENTION

Figure 1:
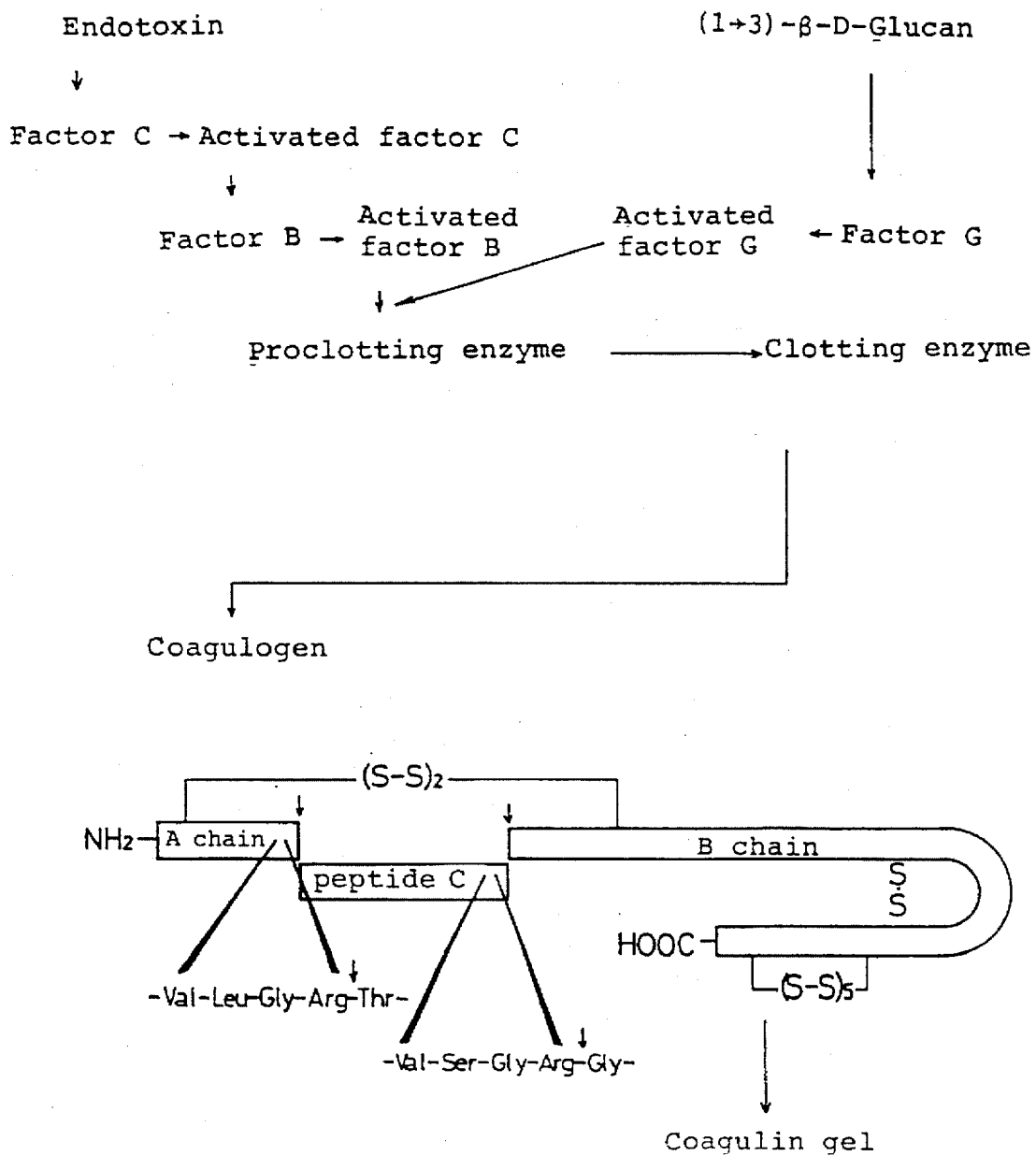
FIG. 1 shows a reaction mechanism of limulus amebocyte lysate with endotoxin and $(1\rightarrow3)$-$\beta$-D-glucan.

The present invention is further illustrated by way of the following Examples, but is not to be construed to be limited thereto.

EXAMPLE 1

500 ml of hemolymph of horseshoe crab (*T. tridentatus*) was centrifuged at 4° C. at 1,500 rpm for 10 minutes. To about 10 g of the resulting precipitate (amebocyte) was added 100 ml of 0.02 M Tris-HCl buffer (pH 8.0), and the mixture was homogeneously fractured by means of a homogenizer [Polytron R PT10 (trade name), manufactured by Kinematica], followed by extraction. The resulting extract was then centrifuged under cooling at 10,000×G for 30 minutes to thereby collect the supernatant and the precipitate. The precipitate was further extracted with 60 ml portions of the buffer twice to finally obtain 200 ml of the lysate.

Five reagents were prepared by the following methods and reactivities of these reagents with endotoxin and $(1\rightarrow3)$-$\beta$-D-glucan were examined and compared with each other.

Reagent I-A was an untreated lysate reagent which was prepared by adding 880 μl of the lysate to a mixture of 200 μl of 0.8 M magnesium chloride with 200 μl of 6 mM Boc-Leu-Gly-Arg-pNA (hereinafter "MS mixture"), followed by lyophilization.

Reagent I-B was a lysate reagent of the present invention (a lysate treated with nylon membrane) which was obtained by passing 1.2 ml of the lysate through a nylon membrane filter of a pore size of 0.20 μm [Nalgene Syringe Filter (trade name), 25 mm in diameter, manufactured by Nalge], adding 880 μl of the filtrate (passed fraction) to the MS mixture and then lyophilizing.

Reagent I-C was a comparative processed lysate which was obtained by passing 1.2 ml of the lysate through a poly(vinylidene fluoride) membrane filter of a pore size of 0.22 μm [Millex GV (trade name, 25 mm in diameter, manufactured by Millipore], adding 880 μl of the filtrate (passed fraction) to the MS mixture and lyophilizing.

Reagent I-D was a comparative processed lysate which was obtained by passing 1.2 ml of the lysate through a polytetrafluoroethylene membrane filter of a pore size of 0.20 μm [Millex FG (trade name), 25 mm in diameter, manufactured by Millipore], adding 880 μl of the filtrate (passed fraction) to the MS mixture and lyophilizing.

Reagent I-E was a comparative processed lysate which was obtained bypassing 1.2 ml of the lysate through a polysulfone membrane filter of a pore size of 0.20 μm [Acrodisc (trade name), 25 mm in diameter, manufactured by Gelman Sciences], adding 880 μl of the filtrate (passed fraction) to the MS mixture and lyophilizing.

To each of the above-mentioned five reagents was added 2.2 ml of 0.2 M Tris-HCl buffer (pH 8.0) and dissolved. To 0.1 ml of the thus-obtained solution was added 0.1 ml portion of endotoxin or $(1\rightarrow3)$-$\beta$-D-glucan and the mixture was incubated at 37° C. for 30 minutes. Separately, 0.05 ml portion of each sample having 2-fold concentration was added and the resulting mixture was incubated in the same manner. Reactivities of the samples with these five reagents were determined by successively adding 0.5 ml of 0.04% sodium nitrite in 0.48 M hydrochloric acid, 0.5 ml of 0.3% ammonium sulfamate and 0.5 ml of 0.07% N-1-naphthylethylenediamine dihydrochloride to incubated mixture and reacting them with pNA (p-nitroaniline) formed after 30 minutes so as to develop color and then measuring the absorbance of the solution at 545 nm.

Table 1 shows the results. The results indicate that $(1\rightarrow3)$-$\beta$-D-glucan can be specifically assayed without suffering from any influence of endotoxin by using the limulus amebocyte lysate which has been once passed through a polyamide membrane (nylon membrane) filter.

TABLE 1

| | | Reactivity ($\Delta A545$ nm/30 min) | | |
|---|---|---|---|---|
| | Reagent | Glucan* | Endotoxin** | Glucan + Endotoxin |
| I-A | (untreated) | 0.225 | 0.420 | 0.647 |
| I-B | (nylon membrane) | 0.342 | 0.001 | 0.343 |
| I-C | (poly(vinylidene fluoride) membrane) | 0.225 | 0.417 | 0.644 |
| I-D | (polytetrafluoro-ethylene membrane) | 0.106 | 0.298 | 0.408 |
| I-E | (polysulfone membrane) | 0.218 | 0.326 | 0.545 |

*: $(1\rightarrow3)$-$\beta$-D-glucan (3 pg/tube).
**: derived from *E. coli* 0111:B4 (2.5 pg/tube).
*Preparation of $(1\rightarrow3)$-$\beta$-D-glucan:

In accordance with International Patent Publication No. WO90/02951 (1990), 1 g of curdlan (commercially available from Wako Pure Chemical industries) was suspended in about 100 ml of 5 mM NaOH aqueous solution and disintegrated by sonicating with a Sonicator™ [Model 5202 PZT (Ohtake Seisakusho, Tokyo] at 20 kHz and 80 W under ice-cooling for 12 minutes. To the treated suspension was added 5 M NaOH aqueous solution so as to give a final concentration of 0.3 M NaOH aqueous solution. The resulting solution was fractionated by gel permeation chromatography (GPC column: two TSK gel G3000 $PW_{xL}$, one G2500 $PW_{xL}$, mobile phase: 0.3 M NaOH aqueous solution, flow rate: 0.5 ml/min). A purified GPC fraction ($(1\rightarrow3)$-$\beta$-D-glucan preparation) of a molecular weight of 216,000 was obtained by re-chromatography.

EXAMPLE 2

To 40 ml of the Starting lysate prepared in Example 1 was added the same amount of distilled water (hereinafter lysate+DW). To 40 ml of the lysate was added the same amount of 15% (w/v) dextran (molecular weight: 40,000) aqueous solution and the mixture was centrifuged at 3,500 rpm for 10 minutes to obtain the supernatant (hereinafter lysate+Dx).

Four reagents were prepared by the following methods and reactivities of these reagents against endotoxin and $(1\rightarrow3)$-$\beta$-D-glucan were examined and compared with each other.

Reagent I-F was an untreated lysate reagent (untreated+DW) which was prepared by adding 1.76 ml of lysate+DW to the MS mixture and lyophilizing.

Reagent I-G was an untreated lysate reagent containing dextran (untreated+Dx) which was prepared by adding 1.76 ml of lysate+Dx to the MS mixture and lyophilizing.

Reagent I-H was a lysate reagent of the present invention (nylon membrane+DW) which was prepared by passing 5.0 ml of lysate+DW through a nylon membrane filter of a pore size of 0.20 μm (Nalgene Syringe Filter), adding 1.76 ml of the filtrate (passed fraction) to the MS mixture and lyophilizing.

Reagent I-I was a lysate reagent of the present invention containing dextran (nylon membrane+Dx) which was prepared by passing 5.0 ml of lysate+Dx through a nylon membrane filter of a pore size of 0.20 μm (Nalgene Syringe Filter), adding 1.76. ml of the filtrate (passed fraction) to the MS mixture and lyophilizing.

Reactivities of each sample with the above-mentioned four reagents were determined in the same manner as in Example 1. Table 2 shows the results. The results indicate that the adsorption of endotoxin-sensitive factors by the carrier can be promoted by previously adding dextran to the lysate and that the sensitivity of the processed lysate thus obtained to $(1\rightarrow3)$-$\beta$-D-glucan can be extremely elevated thereby.

TABLE 2

| | | Reactivity ($\Delta A545$ nm/30 min) | | |
|---|---|---|---|---|
| | Reagent | Glucan* | Endotoxin** | Glucan + Endotoxin |
| I-F | (untreated + DW) | 0.219 | 0.412 | 0.634 |
| I-G | (untreated + Dx) | 0.221 | 0.416 | 0.639 |
| I-H | (nylon membrane + DW) | 0.336 | 0.046 | 0.384 |
| I-I | (nylon membrane + Dx) | 0.510 | 0.001 | 0.510 |

*: $(1\rightarrow3)$-$\beta$-D-glucan (3 pg/tube).
**: derived from *E. coli* 0111:B4 (2.5 pg/tube).

EXAMPLE 3

600 ml of hemolymph of horseshoe crab (*L. polyphemus*) was centrifuged at 4° C. at 1,500 rpm for 10 minutes. To about 12 g of the resulting precipitate (amebocyte) was added 120 ml of 0.02 M Tris-HCl buffer (pH 8.0), and the mixture was homogeneously fractured by means of a homogenizer (Polytron R PT10), followed by extraction. The extract was then centrifuged under cooling at 10,000×G for 30 minutes to thereby collect the supernatant and the precipitate. The precipitate was further extracted with 65 ml portions of the buffer twice to finally obtain 220 ml of the lysate. To 20 ml of this lysate was added the same amount of 15% (w/v) dextran (molecular weight: 70,000) and the mixture was centrifuged at 3,500 rpm for 10 minutes. The supernatant was referred to as D-lysate. Using this D-lysate, two reagents were prepared by the following methods and reactivities of these reagents with endotoxin and $(1\to 3)$-$\beta$-D-glucan were examined and compared with each other.

Reagent I-J was an untreated lysate reagent containing dextran (untreated+Dx) which was prepared by adding 1.76 ml of the D-lysate to the MS mixture and lyophilizing.

Reagent I-K was a lysate reagent of the present invention containing dextran (nylon membrane+Dx) which was prepared by passing 10 ml of the D-lysate through a nylon membrane filter [Nalgene Media Plus Filter Unit (trade name), 90 mm in diameter, manufactured by Nalge], adding 1.76 ml of the filtrate (passed fraction) to the MS mixture and lyophilizing.

Reactivities of each sample with the above-mentioned two reagents were determined in the same manner as in Example 1. Table 3 shows the results. The results indicate that the processed lysate prepared by passing through the polyamide (nylon) membrane reacted not with endotoxin but exclusively with $(1\to 3)$-$\beta$-D-glucan and that the sensitivity of the lysate to $(1\to 3)$-$\beta$-D-glucan can be extremely elevated by adding dextran to the lysate prior to the treatment.

TABLE 3

| | | Reactivity ($\Delta$A545 nm/30 min) | | |
|---|---|---|---|---|
| Reagent | | Glucan* | Endotoxin** | Glucan + Endotoxin |
| I-J | (untreated + Dx) | 0.192 | 0.383 | 0.578 |
| I-K | (nylon membrane + Dx) | 0.423 | 0.000 | 0.423 |

*: $(1\to 3)$-$\beta$-D-glucan (3 pg/tube).
**: derived from *E. coli* 0111:B4 (2.5 pg/tube).

EXAMPLE 4

Preparation of reagent for determining $(1\to 3)$-$\beta$-D-glucan using marketed gelation-utilizing limulus test reagent:

The desired reagents for determining $(1\to 3)$-$\beta$-D-glucan were easily prepared starting from marketed lysate products, i.e., gelation-utilizing limulus test reagents by the following method.

Reagent I-L was a lysate reagent of the present invention (nylon membrane+DW) which was prepared by dissolving a limulus test reagent [Pregel-M (trade name), Lot. AB-01, commercially available from Seikagaku Corporation] in 2.6 ml of distilled water for injection, passing the solution through a nylon membrane filter of a pore size of 0.20 μm [Tissue Culture Filter Unit TC (trade name), 47 mm in diameter, manufactured by Nalge] and using the filtrate (passed fraction) thus obtained.

Reagent I-M was an untreated Pregel-M reagent (untreated+DW).

Reagent I-N was a lysate reagent of the present invention (nylon membrane+DW) which was prepared by dissolving a limulus test reagent [Limulus HSII-Test Wako (trade name), Lot. EMM090, commercialy Available from Wako Pure Chemical Industries] in 5.0 ml of distilled water for injection, passing the solution through the same nylon membrane filter (Tissue Culture Filter Unit TC) and lyophilizing 2.6 ml of the filtrate (passed fraction) thus obtained.

Reagent I-O was an untreated Limulus HSII-Test Wako reagent (untreated+DW).

The reagents I-M and I-N were dissolved in 2.6 ml portions of distilled water for injection, while the reagents I-O was dissolved in 5.0 ml of distilled water for injection. To 0.1 ml of each of the reagents I-L to I-O were added 0.1 ml portions of distilled water for injection (blank), endotoxin (derived from *E. coli* 0111:B4) and $(1\to 3)$-$\beta$-D-glucan. After allowing the mixtures to stand under incubation at 37° C. for 60 minutes, the gelation was examined. Table 4 shows the results. In Table 4, +means a gel was formed while −means no gel was formed. As Table 4 clearly shows, the reagents I-L and I-N are lysates suitable for the purpose of the present invention since they would react exclusively with $(1\to 3)$-$\beta$-D-glucan.

TABLE 4

| $(1\to 3)$-$\beta$-D-glucan (ng/ml) | 0 | 0.1 | 1 | 10 | 100 | 1,000 |
|---|---|---|---|---|---|---|
| I-L: (nylon membrane + DW) | − | − | − | + | + | + |
| I-M: (untreated + DW) | − | − | − | + | + | + |
| Endotoxin (ng/ml) | 0 | 0.001 | 0.01 | 0.1 | 10 | 1,000 |
| I-L: (nylon membrane + DW) | − | − | − | − | − | − |
| I-M: (untreated + DW) | − | − | − | + | + | + |
| $(1\to 3)$-$\beta$-D-glucan (ng/ml) | 0 | 0.1 | 1 | 10 | 100 | 1,000 |
| I-N: (nylon membrane + DW) | − | − | − | + | + | + |
| I-O: (untreated + DW) | − | − | − | + | + | + |
| Endotoxin (ng/ml) | 0 | 0.001 | 0.01 | 0.1 | 10 | 1,000 |
| I-N: (nylon membrane + DW) | − | − | − | − | − | − |
| I-O: (untreated + DW) | − | − | + | + | + | + |

It is known that $(1\to 3)$-$\beta$-D-glucan is a polysaccharide constructing the cell wall of mycetes. Thus the in vivo presence of mycetes can be examined by assaying $(1\to 3)$-$\beta$-D-glucan in vitro. In the following Examples 5 to 7, the methods for detecting mycetes according to the present invention are described.

EXAMPLE 5

Assay of plasma specimen

Blood was aseptically collected from eleven hospitalized patients, who suffered from serious hemopathy (acute llymphoblastic leukemia, acute myelogenous leukemia, multiple myeloma, etc.) and were suspected to suffer from septicemia, and heparin was added to the plasma to serve as a sample. Each sample was centrifuged at 4° C., at 150×G for 10 minutes to obtain platelet-rich plasma. To 0.1 ml of the same was added 0.2 ml of 0.32 M perchloric acid and the mixture was incubated at 37° C. for 20 minutes. Thereafter, a deposit was removed by centrifugation (3,000 rpm, 10 minutes). 0.05 ml of the supernatant was neutralized by adding 0.05 ml of 0.18 M NaOH. This was used as a specimen.

Figure 2:
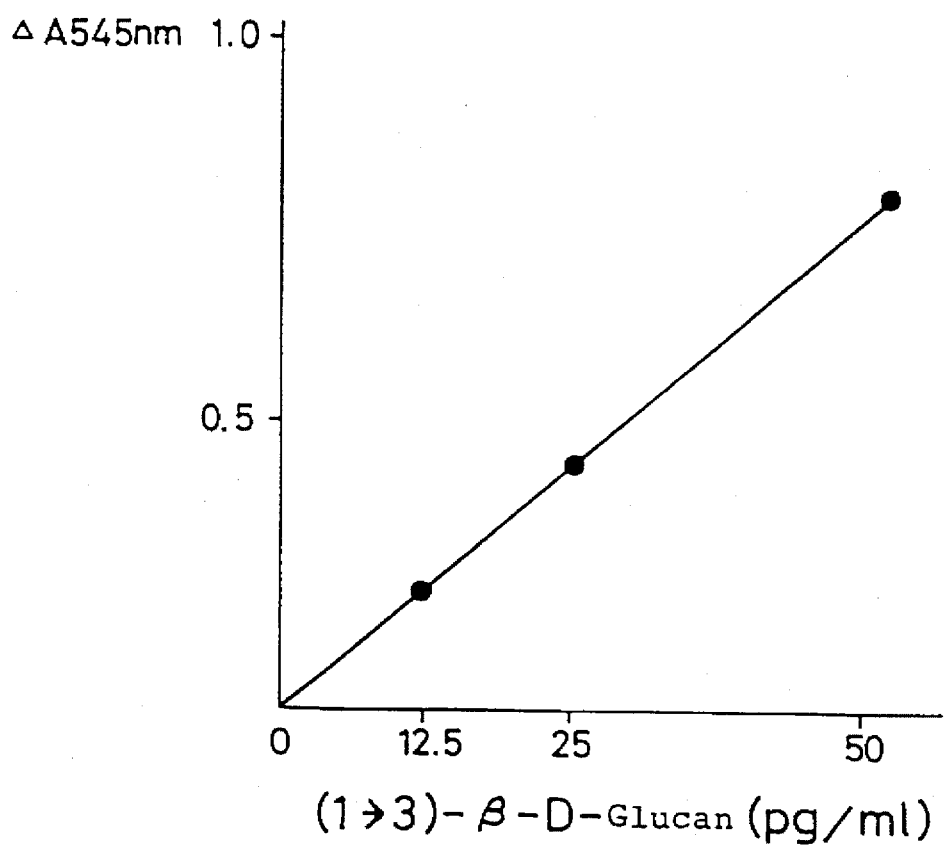
FIG. 2 shows a calibration curve of the reagent I—I against $(1\rightarrow3)$-$\beta$-D-glucan.

Subsequently, 0.1 ml of the reagent I-I for determining $(1\to 3)$-$\beta$-D-glucan according to the present invention prepared by the method described in Example 2 was added thereto, and the mixture was incubated at 37° C. for 30 minutes. To the resulting solution were successively added 0.5 ml of 0.04% sodium nitrite in 0.48 M hydrochloric acid, 0.5 ml of 0.3% ammonium sulfamate and 0.5 ml of 0.07% N-1-naphthylethylenediamine dihydrochloride to effect diazo-coupling. Then, the absorbance of the resulting solution was measured at 545 nm. The amount of (1→3)-β-D-glucan was shown by a calibration curve (FIG. 2) which was separately prepared. As shown in Table 5, a high concentration of (1→3)-β-D-glucan was detected in all of the cases (No. 1 to No. 11) (healthy subjects: 0.2±0.3 pg/ml). In five cases (No. 1 to NO. 5) among them, *Candida albicans, Candida quilliermondii, Candida tropicalis, Candida krusei* and *Cryptococcus neoformans* were respectively detected by blood agar culture. The other two cases (No. 6 and No. 7) were negative by blood agar culture, but *Asperqillus fumiqatus* was detected by a histopathological examination in autopsy. The remaining four cases (No. 8 to No. 11) were negative by blood agar culture, though it was strongly suspected that these cases suffered from mycosis in view of clinical symptoms, progress and drug sensitivity. However, administration of antimycotic agents (amphotericin B, miconazole and fluconazole) resulted in remarkable amelioration in view of clinical symptoms in all cases. Thus, it could be understood that the assay reagent according to the present invention is expected to be highly effective for a rapid diagnosis for mycosis, especially deep mycosis which is hardly detected by conventional test methods.

TABLE 5

(1→3)-β-D-glucan concentration in plasma from patients suffering from opportunistic deep mycosis

| No. | Age/Sex | Disease | Granulocyte number (/μl) | Plasma (1→3)-β-D-glucan (pg/ml) | Blood agar culture | Clinical symptom | Prognosis |
|---|---|---|---|---|---|---|---|
| 1 | 53/F | ALL | 0 | 309.0 | (+) | Isolation of *Candida albicans* | Death |
| 2 | 72/F | MM | 960 | 420.3 | (+) | Isolation of *Candida quilliermondii* | Alive |
| 3 | 61/M | AML | 0 | 28.5 | (+) | Isolation of *Candida tropicalis* | Death |
| 4 | 45/M | APML | 0 | 99.2 | (+) | Isolation of *Candida krusei* | Alive |
| 5 | 59/M | AIHA | 2560 | 521.7 | (+) | Isolation of *Cyptococcus neoformans* | Alive |
| 6 | 48/F | ALL | 0 | 48.5 | (−) | Systemic Aspergillosis (autopsy) | Death |
| 7 | 65/F | APML | 0 | 139.4 | (−) | Systemic Aspergillosis (autopsy) | Death |
| 8 | 45/F | AML | 6278 | 663.8 | (−) | Improved by fluconazole | Alive |
| 9 | 52/M | ALL | 6 | 76.5 | (−) | Improved by miconazole | Alive |
| 10 | 32/M | AML | 1 | 38.7 | (−) | Improved by miconazole | Alive |
| 11 | 29/F | ALL | 0 | 286.1 | (−) | Improved by amphotericin B | Alive |

ALL: acute lymphoblastic leukemia
APML: acute promyelocytic leukemia
AIHA: autoimmune hemolytic anemia
AML: acute myelogenous leukemia
MM: multiple myeloma

EXAMPLE 6

Assay of urine specimen (1→3)-β-D-glucan in urine of three patients suffering from a complicated urinary tract infectious disease in a hospital, from whom *Candida albicans* or *Candida glabrata* was detected by urinary culture, was determined using the reagent of the present invention. Intermediate urine was aseptically collected in a sterilized cup. To 0.005 ml of the urine was added 0.1 ml of distilled water for injection and then 0.1 ml of the reagent I-B of the invention for determining (1→3)-β-D-glucan prepared according to the method described in Example 1, followed by incubating at 37° C. for 30 minutes. After diazo-coupling as effected in Example 5, the absorbance of the resulting solution was measured at 545 rim. The amount of (1→3)-β-D-glucan was calculated from a calibration curve which had been separately prepared. As shown in Table 6, a high concentration of (1→3)-β-D-glucan was detected (healthy subjects: 10 pg/ml or less) in all of three cases. Thus it can be understood that the reagent of the present invention is expected to be highly effective for a rapid diagnosis for mycotic urinary tract infectious diseases.

TABLE 6

(1→3)-β-D-glucan concentration in mycete-infected urine

| No. | Detected mycete | CFU/ml | (1→3)-β-D-glucan (ng/ml) |
|---|---|---|---|
| 1 | *Candida albicans* | >10⁴ | 28.5 |
| 2 | *Candida albicans* | >10⁴ | 12.5 |
| 3 | *Candida glabrata* | >10⁴ | 18.0 |

EXAMPLE 7

Assay of cerebrospinal fluid specimen

The cerebrospinal fluid was aseptically collected by means of lumber puncture from three patients who were suspected to suffer from meningitis in a hospital and were confirmed to suffer from mycotic meningitis by detecting *Cryptococcus neoformans* in cerebrospinal fluid. To 0.05 ml of the cerebrospinal fluid were added 0.05 ml of distilled water for injection and 0.1 ml of the reagent I-K of the present invention for determining (1→3)-β-D-glucan described in Example 3 and the mixture was incubated at 37° C. for 30 minutes. After diazo-coupling as effected in Example 5, the absorbance of the resulting solution was measured at 545 nm. The amount of (1→3)-β-D-glucan was calculated from a calibration curve which had been separately prepared., As Table 7 shows, a high concentration of (1→3)-β-D-glucan was detected (healthy subjects: 1 pg/ml or less) in all of three cases. Thus it can be understood that the reagent of the present invention is expected to be highly effective for an early rapid diagnosis for mycotic meningitis.

TABLE 7

(1→3)-β-D-glucan concentration in mycete-infected cerebrospinal fluid

| No. | Detected mycete | (1→3)-β-D-glucan (pg/ml) |
|---|---|---|
| 1 | *Cryptococcus neoformans* | 136.2 |
| 2 | *Cryptococcus neoformans* | 58.7 |
| 3 | *Cryptococcus neoformans* | 105.1 |

EXAMPLE 8

Using the raw lysate prepared by the method as described in Example 1, four reagents were prepared by the following methods and reactivities of these reagents with endotoxin and (1→3)-β-D-glucan were examined and compared with each other.

Reagent II-A was an untreated lysate reagent (untreated) which was prepared by adding 880 μl of the lysate to the MS mixture, followed by lyophilization.

Reagent II-B was a lysate reagent of the present invention (cellulose ester membrane) which was obtained by passing 1.5 ml of the lysate through a cellulose ester membrane filter of a pore size of 0.22 μm [Sterifil D-GS (tradename), cellulose acetate/cellulose nitrate mixture, 47 mm in diameter, manufactured by Millipore], adding 880 μl of the filtrate (passed fraction) to the MS mixture and then lyophilizing.

Reagent II-C was a lysate reagent of the present invention (cellulose acetate membrane) which was obtained by passing 1.5 ml of the lysate through a cellulose acetate membrane filter of a pore size of 0.20 μm [Nalgene Filterware (trade name), 47mmin diameter, manufactured by Nalge], adding 880 μl of the filtrate (passed fraction) to the MS mixture and lyophilizing.

Reagent II-D was a lysate reagent of the present invention (cellulose nitrate membrane) which was obtained by passing 1.5 ml of the lysate through a cellulose nitrate membrane filter of a pore size of 0.20 μm [Nalgene Filterware (trade name), 47 mmin diameter, manufactured by Nalge], adding 880 μl of the filtrate (passed fraction) to the MS mixture and lyophilizing.

Reactivities of each sample with the above-mentioned four reagents were determined in the same manner as in Example 1.

Table 8 shows the results. The results indicate that (1→3)-β-D-glucan can be quantitatively and specifically determined without suffering from any influence of endotoxin by using the lysate which has been once passed through a cellulose membrane filter.

TABLE 8

| Reagent | | Pore size (μm) | Reactivity (ΔA545 nm/30 min) | | |
|---|---|---|---|---|---|
| | | | Glucan* | Endotoxin** | Glucan + Endotoxin |
| II-A | (untreated) | — | 0.226 | 0.409 | 0.638 |
| II-B | (cellulose ester membrane) | 0.22 | 0.349 | 0.004 | 0.354 |
| II-C | (cellulose acetate membrane) | 0.20 | 0.345 | 0.002 | 0.348 |
| II-D | (cellulose nitrate membrane) | 0.20 | 0.343 | 0.001 | 0.345 |

*: (1→3)-β-D-glucan (3 pg/tube).
**: derived from E. coli 0111:B4 (2.5 pg/tube).

EXAMPLE 9

Using the lysate+DW prepared in Example 2, six reagents were prepared by the following methods and reactivities of these reagents with endotoxin and (1→3)-β-D-glucan were examined and compared with each other.

Reagent II-E was an untreated lysate reagent (lysate+DW) which was prepared by adding 1.76 ml of lysate+DW to the MS mixture and lyophilizing.

Reagent II-F was an untreated lysate reagent containing dextran (lysate+Dx) which was prepared by adding 1.76 ml of lysate+Dx to the MS mixture and lyophilizing.

Reagent II-G was a lysate reagent of the present invention (cellulose ester membrane+DW) which was prepared by passing 5 ml of lysate+DW through a cellulose ester membrane filter of a pore size of 0.22 μm [Millex GS (trade name), cellulose acetate/cellulose nitrate mixture, 25 mm in diameter, manufactured by Millipore], adding 1.76 ml of the filtrate (passed fraction) to the MS mixture and lyophilizing.

Reagent II-H was a lysate reagent of the present invention containing dextran (cellulose ester membrane+Dx) which was prepared by passing 5 ml of lysate+Dx through a cellulose ester membrane filter of a pore size of 0.22 μm (Millex GS), adding 1.76 ml of the filtrate (passed fraction) to the MS mixture and lyophilizing.

Reagent II-I was a lysate reagent of the present invention (cellulose acetate membrane+DW) which was prepared bypassing 5 ml of lysate+DW through a cellulose acetate membrane filter of a pore size of 0.20 μm [Nalgene Syringe Filter (trade name), 25 mm in diameter, manufactured by Nalge], adding 1.76 ml of the filtrate (passed fraction) to the MS mixture and lyophilizing.

Reagent II-J was a lysate reagent of the present invention containing dextran (cellulose acetate membrane+Dx) which was prepared by passing 5 ml of lysate+Dx through a cellulose acetate membrane filter of a pore size of 0.20 μm (Nalgene Syringe Filter), adding 1.76 ml of the filtrate (passed fraction) to the MS mixture and lyophilizing.

Reactivities of each sample with the above-mentioned six reagents were determined by the method as described in Example 1. Table 9 shows the results. The results indicate that the adsorption of endotoxin-sensitive factors by the carrier can be promoted by previously adding dextran to the lysate and that the sensitivity of the processed lysate thus obtained to (1→3)-β-D-glucan can be extremely elevated thereby.

TABLE 9

| Reagent | | Pore size (μm) | Reactivity (ΔA545 nm/30 min) | | |
|---|---|---|---|---|---|
| | | | Glucan* | Endotoxin** | Glucan + Endotoxin |
| II-E | (untreated + Dw) | — | 0.226 | 0.411 | 0.640 |
| II-F | (untreated + Dx) | — | 0.227 | 0.417 | 0.646 |
| II-G | (cellulose ester membrane + DW) | 0.22 | 0.347 | 0.046 | 0.396 |
| II-H | (cellulose ester membrane + Dx) | 0.22 | 0.500 | 0.001 | 0.501 |
| II-I | (cellulose acetate membrane + DW) | 0.20 | 0.351 | 0.050 | 0.403 |
| II-J | (cellulose acetate membrane + Dx) | 0.20 | 0.490 | 0.002 | 0.491 |

*: (1→3)-β-D-glucan (3 pg/tube).
**: derived from E. coli 0111:B4 (2.5 pg/tube).

EXAMPLE 10

Using the D-lysate prepared in Example 3, eight reagents were prepared by the following methods and reactivities of these reagents with endotoxin and (1→3)-β-D-glucan were examined and compared with each other.

Reagent II-K was an untreated lysate reagent which was prepared by adding 1.76 ml of the D-lysate to the MS mixture and lyophilizing.

Reagent II-L was a lysate reagent of the present invention (Cellulose gel) which was prepared by mixing 2.6 ml of the D-lysate with the same amount of a porous cellulose gel [Cellulofine GC-200m (trade name), commercially available from Seikagaku Corporation], filtering the mixture through a glass filter (G3), adding 1.76 ml of the filtrate to the MS mixture and lyophilizing.

Reagent II-M was a lysate reagent of the present invention (diethylaminoethylcellulose gel) which was prepared by mixing 2.6 ml of the D-lysate with the same amount of a diethylaminoethylcellulose gel [DEAE-Cellulose, manufactured by Serra Feinbiochemica GmbH], filtering the mixture through a glass filter (G3), adding 1.76 ml of the filtrate to the MS mixture and lyophilizing.

Reagent II-N was a lysate reagent of the present invention (carboxymethylcellulose gel) which was prepared by mixing 2.6 ml of the D-lysate with the same amount of a carboxymethylcellulose gel [manufactured by Serva Feinbio-chemica GmbH], filtering the mixture through a glass filter (G3), adding 1.76 ml of the filtrate to the MS mixture and lyophilizing.

Reagent II-O was a lysate reagent of the present invention (phosphocellulose gel) which was prepared by mixing 2.6 ml of the D-lysate with the same amount of a phosphocellulose gel [manufactured by Serra Feinbiochemica GmbH], filtering the mixture through a glass filter (G3), adding 1.76 ml of the filtrate to the MS mixture and lyophilizing.

Reagent II-P was a comparative lysate reagent (agarose gel) which was prepared by mixing 2.6 ml of the D-lysate with the same amount of an agarose gel [Sepharose CL-6B (trade name), manufactured by Pharmacia], filtering the mixture through a glass filter (G3), adding 1.76 ml of the filtrate to the MS mixture and lyophilizing.

Reagent II-Q was a comparative lysate reagent (dextran gel) which was prepared by mixing 2.6 ml of the D-lysate with the same amount of a dextran gel [Sephadex G-150 (trade name), manufactured by Pharmacia], filtering the mixture through a glass filter (G3), adding 1.76 ml of the filtrate to the MS mixture and lyophilizing.

Reagent II-R was a comparative lysate reagent (polyacrylamide gel) which was prepared by mixing 2.6 ml of the D-lysate with the same amount of a polyacrylamide gel [Bio-Gel P-300 (trade name), manufactured by Bio-Rad Laboratories], filtering the mixture through a glass filter (G3), adding 1.76 ml of the filtrate to the MS mixture and lyophilizing.

Reactivities of each sample with the above-mentioned eight reagents were determined by the method as described in Example 1. Table 10 shows the results. The results indicate that $(1\rightarrow3)$-$\beta$-D-glucan can be specifically and quantitatively determined without affected by endotoxin by using the lysate which have been passed through a cellulose carrier.

TABLE 10

| | | Reactivity ($\Delta A545$ nm/30 min) | | |
|---|---|---|---|---|
| | Reagent | Glucan* | Endotoxin** | Glucan + Endotoxin |
| II-K | (untreated) | 0.197 | 0.379 | 0.580 |
| II-L | (cellulose gel) | 0.438 | 0.000 | 0.438 |
| II-M | (diethylamino-ethylcellulose gel) | 0.431 | 0.004 | 0.436 |
| II-N | (carboxymethyl-cellulose gel) | 0.428 | 0.002 | 0.431 |
| II-O | (phosphocellulose gel) | 0.426 | 0.001 | 0.427 |
| II-P | (agarose gel) | 0.186 | 0.201 | 0.390 |
| II-Q | (dextran gel) | 0.181 | 0.214 | 0.399 |
| II-R | (polyacrylamide gel) | 0.188 | 0.368 | 0.559 |

*: $(1\rightarrow3)$-$\beta$-D-glucan (3 pg/tube).
**: derived from *E. coli* 0111:B4 (2.5 pg/tube).

EXAMPLE 11

Preparation of reagent for determining $(1\rightarrow3)$-$\beta$-D-glucan using marketed gelation-utilizing limulus test reagent:

The desired reagents for determining $(1\rightarrow3)$-$\beta$-D-glucan were prepared starting from marketed lysate products, i.e., gelation-utilizing limulus test reagents by the following method.

Reagent II-L-1 was a lysate reagent of the present invention which was prepared by dissolving a limulus test reagent [Pregel-M (trade name), Lot. AB-01, commercially available from Seikagaku Corporation] in 2.6 ml of distilled water for injection, passing the solution through a cellulose acetate membrane filter of a pore size of 0.22 μm (Nalgene Filterware) and lyophilizing 1.4 ml of the filtrate (passed fraction) thus obtained.

Reagent II-L-2 was an untreated Pregel-M reagent.

Reagent II-L-3 was a lysate reagent of the present invention which was prepared by dissolving a limulus test reagent [Limulus HSII-Test Wako (trade name), Lot. EMM090, commercially available from Wako Pure Chemical Industries] in 5.0 ml of distilled water for injection, passing the solution through a cellulose ester membrane filter (Sterifil D-GS) and using the filtrate thus obtained.

Reagent II-L-4 was an untreated Limulus HSII-Test Wako reagent.

The reagents II-L-1, II-L-2 and II-L-4 were dissolved respectively in 1.4 ml, 2.6 ml and 5.0 ml portions of distilled water for injection. To these reagents were added the same samples as employed in Example 4 and gelation was examined. Table 11 shows the results. In Table 11, + means a gel was formed while − means no gel was formed. As Table 11 clearly shows, the reagents II-L-1 and II-L-3 are lysates suitable for the purpose of the present invention since they reacted exclusively with $(1\rightarrow3)$-$\beta$-D-glucan.

TABLE 11

| $(1\rightarrow3)$-$\beta$-D-glucan (ng/ml) | 0 | 0.1 | 1 | 10 | 100 | 1,000 |
|---|---|---|---|---|---|---|
| II-L-1 | − | − | − | + | + | + |
| II-L-2 | − | − | − | + | + | + |
| Endotoxin (ng/ml) | 0 | 0.001 | 0.01 | 0.1 | 10 | 1,000 |
| II-L-1 | − | − | − | − | − | − |
| II-L-2 | − | − | − | + | + | + |
| $(1\rightarrow3)$-$\beta$-D-glucan (ng/ml) | 0 | 0.1 | 1 | 10 | 100 | 1,000 |
| II-L-3 | − | − | − | + | + | + |
| II-L-4 | − | − | − | + | + | + |
| Endotoxin (ng/ml) | 0 | 0.001 | 0.01 | 0.1 | 10 | 1,000 |
| II-L-3 | − | − | − | − | − | − |
| II-L-4 | − | − | + | + | + | + |

EXAMPLE 12

Assay of plasma specimen

Figure 3:
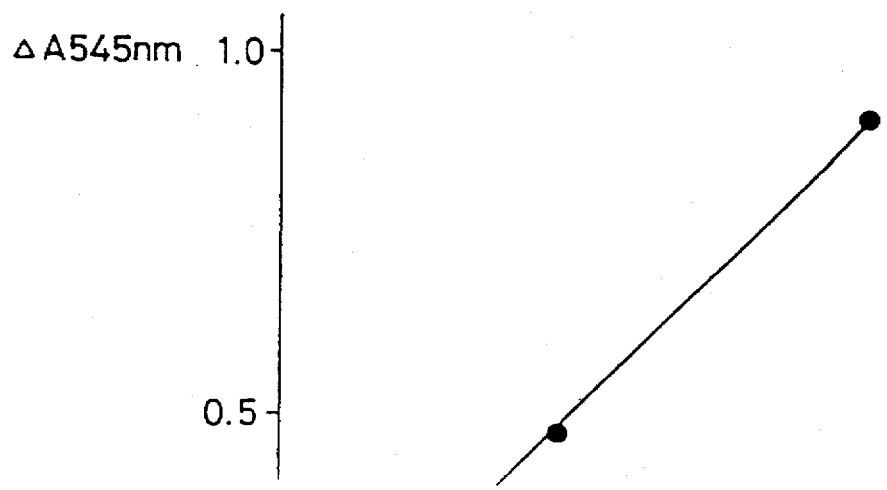
FIG. 3 shows a calibration curve of the reagent II-H against $(1\rightarrow3)$-$\beta$-D-glucan.

Specimens were prepared by the same method as described in Example 5. Subsequently, 0.1 ml of the reagent II-H for determining $(1\rightarrow3)$-$\beta$-D-glucan according to the present invention prepared by the method described in Example 9 was added thereto, and the mixture was incubated at 37° C. for 30 minutes. The resulting reaction mixture was treated in the same manner as in Example 5 and the absorbance of the resulting solution was measured. The amount of $(1\rightarrow3)$-$\beta$-D-glucan was calculated from a calibration curve (FIG. 3) which was separately prepared. As shown in Table 12, a high concentration of $(1\rightarrow3)$-$\beta$-D-glucan was detected in all of the cases (No. 1 to No. 11) (healthy subjects: 0.2±0.3 pg/ml). In five cases (No. 1 to No. 5) among them, *Candida albicans*, *Candida quilliermondii*, *Candida tropicalis*, *Candida krusei* and *Cryptococcus neoformans* were respectively detected by blood agar culture. The other two cases (No. 6 and No. 7) were negative by blood agar culture, but *Aspergillus fumigatus* was detected by a histopathological examination in autopsy. The remaining four cases (No. 8 to No. 11) were negative by blood agar culture, though they were strongly suspected to suffer from mycosis in view of clinical symptoms, progress and drug sensitivity. However, administration of antimycotic agents (amphotericin B, miconazole and fluconazole) resulted in remarkable amelioration in view of clinical symptoms in all cases. Thus, it could be understood that the assay reagent according to the present invention is expected to be highly effective for a rapid diagnosis for mycosis, especially deep mycosis which is hardly detected by conventional test methods.

described in Example 7. Then 0.1 ml of the reagent II-L of the present invention for determining (1→3)-β-D-glucan prepared in Example 10 was added thereto and the mixture was incubated at 37° C. for 30 minutes. After diazo-coupling as effected in Example 5, the absorbance of the resulting solution was measured at 545 nm. The amount of (1→3)-β-D-glucan was calculated from a calibration curve which had been separately prepared. As Table 14 shows, a high concentration of (1→3)-β-D-glucan was detected (healthy subjects: 1 pg/ml or less) in all of three cases. Thus it can be understood that the assay method using the reagent of the

TABLE 12

(1→3)-β-D-glucan concentration in plasma from patients suffering from opportunistic deep mycosis

| No. | Age/Sex | Disease | Granulocyte number (/μl) | Plasma (1→3)-β-D-glucan (pg/ml) | Blood agar culture | Clinical symptom | Prognosis |
|---|---|---|---|---|---|---|---|
| 1 | 53/F | ALL | 0 | 325.2 | (+) | Isolation of Candida albicans | Death |
| 2 | 72/F | MM | 960 | 415.0 | (+) | Isolation of Candida quilliermondii | Alive |
| 3 | 61/M | AML | 0 | 22.7 | (+) | Isolation of Candida tropicalis | Death |
| 4 | 45/M | APML | 0 | 86.8 | (+) | Isolation of Candida krusei | Alive |
| 5 | 59/M | AIHA | 2560 | 540.2 | (+) | Isolation of Cyptococcus neoformans | Alive |
| 6 | 48/F | ALL | 0 | 50.5 | (−) | Systemic Aspergillosis (autopsy) | Death |
| 7 | 65/F | APML | 0 | 138.7 | (−) | Systemic Aspergillosis (autopsy) | Death |
| 8 | 45/F | AML | 6278 | 669.9 | (−) | Improved by fluconazole | Alive |
| 9 | 52/M | ALL | 6 | 76.8 | (−) | Improved by miconazole | Alive |
| 10 | 32/M | AML | 1 | 38.7 | (−) | Improved by miconazole | Alive |
| 11 | 29/F | ALL | 0 | 275.1 | (−) | Improved by amphotericin B | Alive |

ALL: acute lymphoblastic leukemia
APML: acute promyelocytic leukemia
AIHA: autoimmune hemolytic anemia
AML: acute myelogenous leukemia
MM: multiple myeloma

EXAMPLE 13
Assay of urine specimen

Urine specimens were prepared from patients suffering from an urinary tract infectious disease in the same manner as in Example 6. To the urine was added 0.1 ml of the reagent II-C of the present invention for determining (1→3)-β-D-glucan prepared by the method described in Example 8, followed by incubating at 37° C. for 30 minutes. After diazo-coupling as effected in Example 5, the absorbance of the resulting solution was measured at 545nm. The amount of (1→3)-β-D-glucan was calculated from a calibration curve which had been separately prepared. As shown in Table 13, a high concentration of (1→3)-β-D-glucan was detected (healthy subjects: 10 pg/ml or less) in all of three cases. Thus it can be understood that the assay method using the reagent of the present invention is expected to be highly effective for a rapid diagnosis for mycotic urinary tract infectious diseases.

TABLE 13

(1→3)-β-D-glucan concentration in mycete-infected urine

| No. | Detected mycete | CFU/ml | (1→3)-β-D-glucan (ng/ml) |
|---|---|---|---|
| 1 | Candida albicans | >10⁴ | 27.5 |
| 2 | Candida albicans | >10⁴ | 12.9 |
| 3 | Candida glabrata | >10⁴ | 17.8 |

EXAMPLE 14
Assay of cerebrospinal fluid specimen

Cerebrospinal fluid specimens were prepared from patients suffering from meningitis by the method as present invention is expected to be highly effective for an early rapid diagnosis for mycotic meningitis.

TABLE 14

| | (1→3)-β-D-glucan concentration in mycete-infected cerebrospinal fluid | |
|---|---|---|
| No. | Detected mycete | (1→3)-β-D-glucan (pg/ml) |
| 1 | Cryptococcus neoformans | 138.5 |
| 2 | Cryptococcus neoformans | 60.8 |
| 3 | Cryptococcus neoformans | 105.5 |

Industrial Applicability

The present invention provides an endotoxin-sensitive factor-free reagent for specifically determining (1→3)-β-D-glucan using lysate and an assay method using said reagent. According to the present invention, (1→3)-β-D-glucan of mycotic origin contained in biological specimens such as blood or urine can be rapidly and easily determined at a high accuracy. Thus the present invention is applicable to a rapid diagnosis, an appropriate therapy and evaluation of therapeutic effect of deep mycosis which can be hardly detected by conventional test methods such as mycete culture.

Further, the reagent of the present invention makes it possible to rapidly and accurately determine (1→3)-β-D-glucan of mycotic origin which contaminates distilled water for injection, parenteral drugs and medical devices. Furthermore, the reagent of the present invention can be applied to screening of (1→3)-β-D-glucan having antitumor activity.

We claim:

1. A method for producing a reagent for determining (1→3)-β-D-glucan which comprises treating a limulus amebocyte lysate-containing solution with an adsorbent that specifically adsorbs an endotoxin-sensitive factor, said adsorbent selected from the group consisting of an adsorbent consisting essentially of polyamide and an adsorbent consisting essentially of cellulose, and separating said adsorbent from said treated solution to remove endotoxin-sensitive factors from the limulus amebocyte lysate-containing solution to give a treated limulus amebocyte lysate substantially free from any endotoxin-sensitive factor and containing at least an ingredient capable of specifically reacting with (1→3)-β-D-glucan.

2. A method as claimed in claim 1 wherein water-soluble dextran is added to said limulus amebocyte lysate-containing solution in advance of or in the step of treating said solution with said adsorbent to increase viscosity of said solution.

3. A method as claimed in claim 1, wherein a divalent metal salt effective in the activation of a cascade reaction system is added, optionally together with a substrate of a clotting enzyme, to said treated limulus amebocyte lysate and the resulting mixture is dried under unheated conditions.

4. A method for detecting a mycete comprising (1→3)-β-D-glucan which comprises:
   (a) contacting a body fluid of a patient suffering from mycosis with a reagent for determining (1→3)-β-D-glucan obtained by the method of claim 1 to yield a mixture, wherein (1→3)-β-D-glucan] activates a factor G in said reagent to yield an activated factor G which converts a clotting proenzyme in said reagent to yield a clotting enzyme with amidolytic or proteolytic activity;
   (b) measuring the amidolytic or proteolytic activity in said mixture; and
   (c) correlating the amidolytic or proteolytic activity of said mixture to the presence of a mycete comprising (1→3)-β-D-glucan in said body fluid.

5. A method for determining (1→3)-β-D-glucan in a sample comprising:
   (a) contacting a sample suspected of containing (1→3)-β-D-glucan with a reagent for determining (1→3)-β-D-glucan obtained by the method of claim 1 to yield a mixture, wherein (1→3)-β-D-glucan activates a factor G in said reagent to yield an activated factor G which converts a clotting proenzyme in said reagent to yield a clotting enzyme with amidolytic or proteolytic activity;
   (b) measuring the amidolytic or proteolytic activity in said mixture; and
   (c) correlating the amidolytic or proteolytic activity of said mixture to the amount of (1→3)-β-D-glucan in said sample.

6. A method as claimed in claim 1, wherein said polyamide is nylon and said cellulose is selected from the group consisting of cellulose, cellulose acetate, cellulose nitrate, aminoethylcellulose, bromoacetylcellulose, phosphocellulose, carboxymethylcellulose and carboxymethylcellulose hydrazine derivative.

* * * * *

UNITED STATES PATENT AND TRADEMARK OFFICE
CERTIFICATE OF CORRECTION

PATENT NO.  : 5,681,710
DATED       : 28 October 1997
INVENTOR(S) : Shigenori TANAKA et al.

It is certified that errors appear in the above-identified patent and that said Letters Patent is hereby corrected as shown below:

Column 17, line 29, delete the "]" following "glucan".

Signed and Sealed this

Thirtieth Day of June, 1998

Attest:

BRUCE LEHMAN

*Attesting Officer*   *Commissioner of Patents and Trademarks*